(12) United States Patent
Hochareon et al.

(10) Patent No.: US 7,890,187 B2
(45) Date of Patent: Feb. 15, 2011

(54) LEAD ASSEMBLY HAVING A TETHERED SENSOR AND METHODS RELATED THERETO

(75) Inventors: Pramote Hochareon, St. Paul, MN (US); Bruce Tockman, Scandia, MN (US); Mohan Krishnan, Shoreview, MN (US); Mary Lowden, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 586 days.

(21) Appl. No.: 11/782,333

(22) Filed: Jul. 24, 2007

(65) Prior Publication Data

US 2009/0030331 A1 Jan. 29, 2009

(51) Int. Cl.
*A61N 1/05* (2006.01)

(52) U.S. Cl. ...................................... 607/119

(58) Field of Classification Search ......... 600/380–382, 600/504–505, 518; 607/115–125; 604/104; 128/899
See application file for complete search history.

(56) References Cited

U.S. PATENT DOCUMENTS

| | | | |
|---|---|---|---|
| 3,995,623 A * | 12/1976 | Blake et al. ................ 600/381 |
| 4,600,017 A | 7/1986 | Schroeppel | |
| 4,967,755 A | 11/1990 | Pohndorf et al. | |
| 5,174,303 A | 12/1992 | Schroeppel | |
| 5,324,326 A | 6/1994 | Lubin | |
| 5,353,800 A | 10/1994 | Pohndorf et al. | |
| 5,429,144 A * | 7/1995 | Wilk ........................... 128/898 |
| 5,431,628 A * | 7/1995 | Millar ................... 604/100.01 |
| 5,476,499 A * | 12/1995 | Hirschberg ................. 607/123 |
| 6,309,350 B1 | 10/2001 | VanTassel et al. | |
| 6,312,380 B1 * | 11/2001 | Hoek et al. ................. 600/437 |
| 6,321,380 B1 * | 11/2001 | Derrick et al. .............. 717/168 |
| 6,645,143 B2 | 11/2003 | VanTassel et al. | |
| 6,666,826 B2 | 12/2003 | Salo et al. | |
| 6,743,173 B2 | 6/2004 | Penner et al. | |
| 6,840,956 B1 | 1/2005 | Wolinsky et al. | |
| 6,892,095 B2 * | 5/2005 | Salo ........................... 607/21 |
| 6,970,742 B2 | 11/2005 | Mann et al. | |
| 7,364,566 B2 * | 4/2008 | Elkins et al. ................ 604/104 |
| 7,474,916 B2 * | 1/2009 | Gutierrez .................... 600/518 |
| 2003/0055344 A1 | 3/2003 | Eigler et al. | |
| 2005/0159801 A1 | 7/2005 | Marshall et al. | |

* cited by examiner

*Primary Examiner*—Carl H Layno
*Assistant Examiner*—Paula J Stice
(74) *Attorney, Agent, or Firm*—Faegre & Benson LLP

(57) ABSTRACT

A lead including a tether with a sensor for measuring a physiologic parameter within the body and methods for implanting such devices are disclosed. An illustrative lead includes a lead body with one or more conductors, an electrode, and a tether extending from the lead body including a sensor for measuring a physiologic parameter within the body such as blood pressure, blood chemistry or blood gas. A method of implanting a lead includes disposing a lead body of the lead at a first position within a patient, anchoring the lead body at the first position, flowing a sensor and tether tethered to the lead body to a second position, and measuring a physiologic parameter using the sensor at the second position.

20 Claims, 5 Drawing Sheets

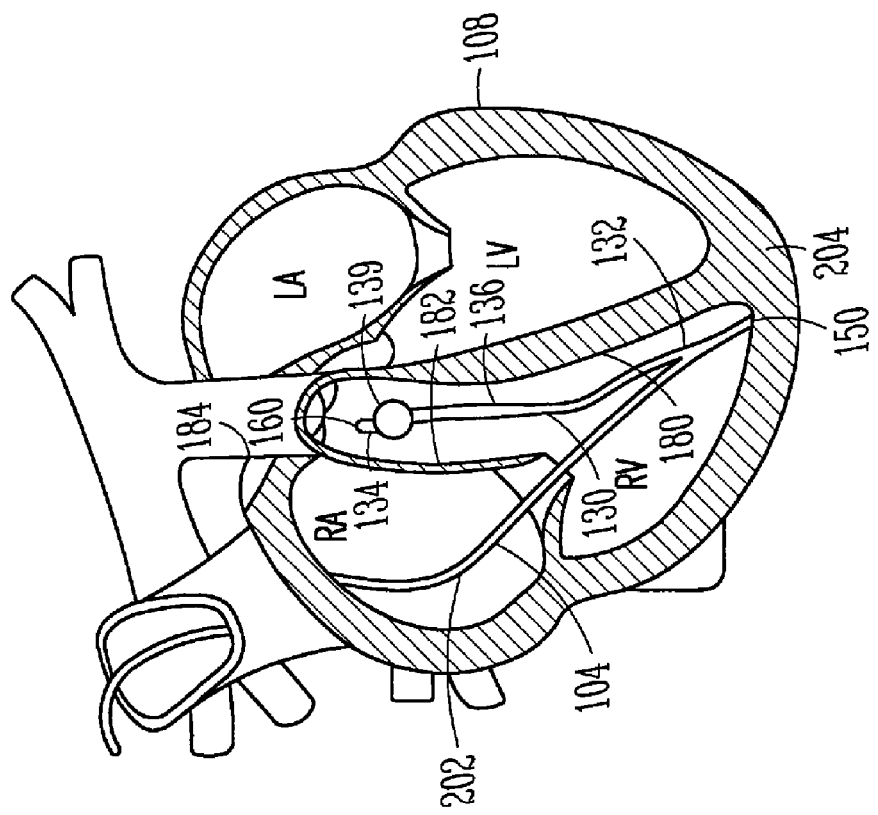
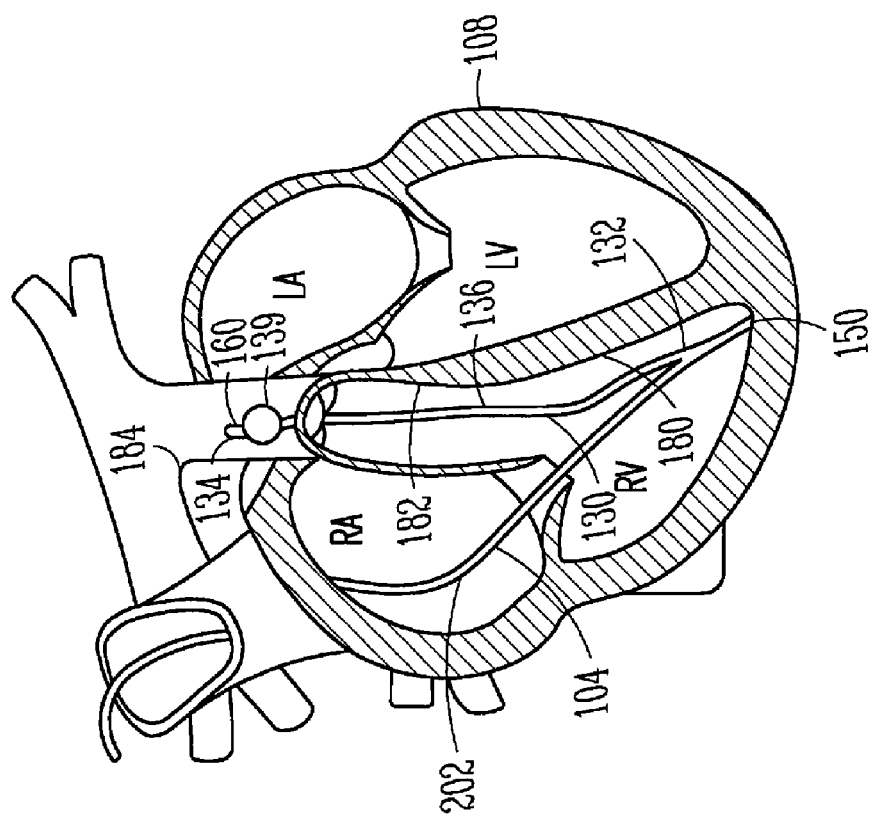
FIG. 2A
FIG. 2B

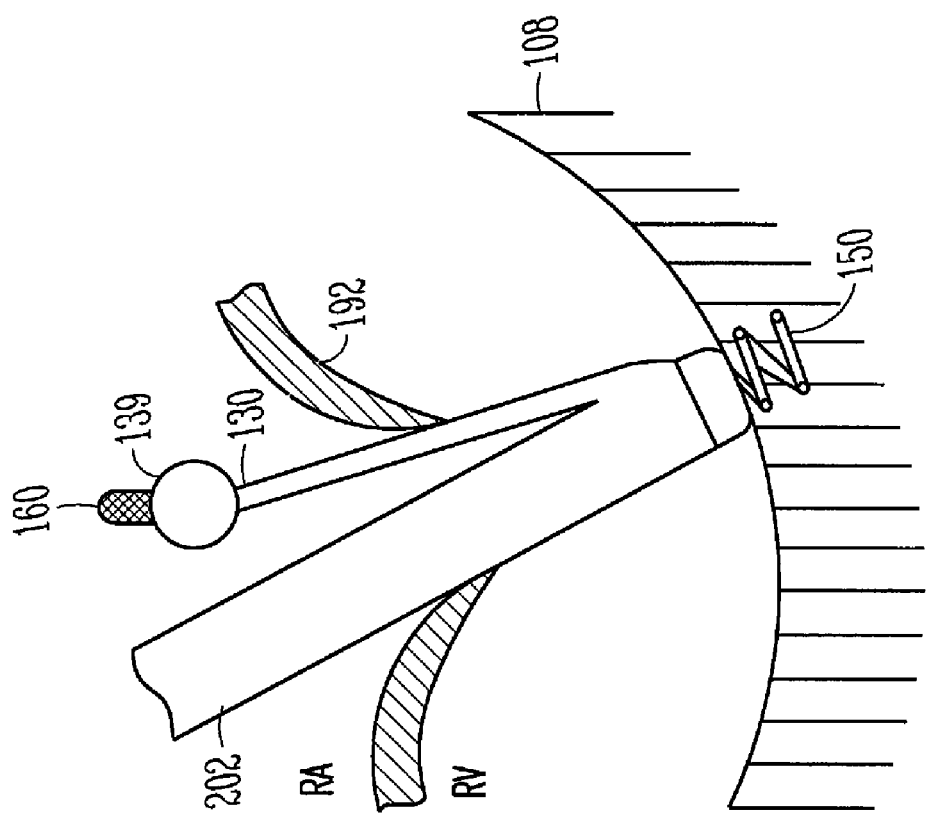
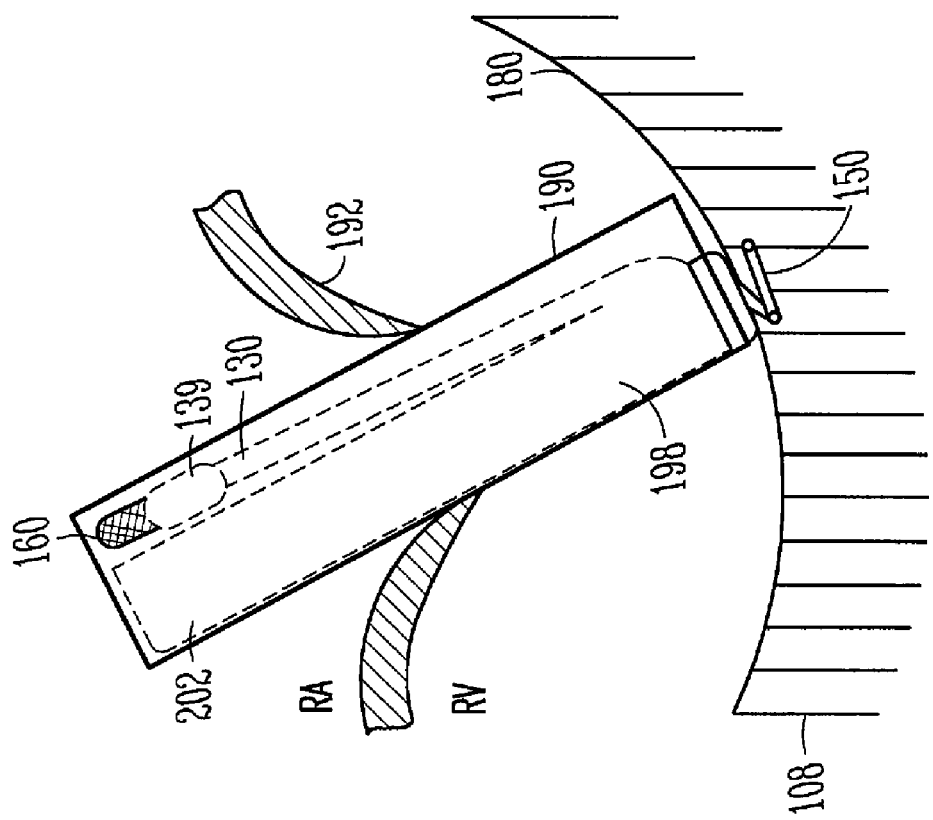

LEAD ASSEMBLY HAVING A TETHERED SENSOR AND METHODS RELATED THERETO

TECHNICAL FIELD

Leads for linking medical devices with selected bodily tissue to be sensed or stimulated by such devices. More particularly, but not by way of limitation, this relates to a lead including a sensor associated therewith.

BACKGROUND

In a condition known as congestive heart failure, the heart cannot provide sufficient blood supply at a time when fluid is being retained in the circulation and interstitial space, as a result of pump failure. When water is retained, workload for the heart increases and oxygen supply to the heart decreases. This results in hemodynamic instability of congestive heart failure. Pulmonary wedge pressure had been used for monitoring of hemodynamic status. However, pulmonary wedge pressure measurement can be an invasive procedure typically done only in cardiac catheter centers.

What is needed is an implantable device that can monitor hemodynamic status.

BRIEF DESCRIPTION OF THE DRAWINGS

In the drawings, like numerals describe substantially similar components throughout the several views. The drawings illustrate generally, by way of example, but not by way of limitation, various embodiments discussed herein.

FIG. 2A is a cross-sectional view of a portion of a lead as constructed in accordance with at least one embodiment.

FIG. 2B is a cross-sectional view of a portion of a lead as constructed in accordance with at least one embodiment.

FIG. 4A is a cross-sectional view of a portion of a lead as constructed in accordance with at least one embodiment.

FIG. 4B is a cross-sectional view of a portion of a lead as constructed in accordance with at least one embodiment.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined, other embodiments may be utilized or structural and logical changes may be made without departing from the scope of the present leads and methods. It is also to be understood that the various embodiments of the present leads and methods, although different, are not necessarily mutually exclusive. For example, a particular feature, structure or characteristic described in one embodiment may be included within other embodiments. The following detailed description is, therefore, not to be taken in a limiting sense, and the scope of the present leads and methods are defined by the appended claims and their legal equivalents.

Figure 1:
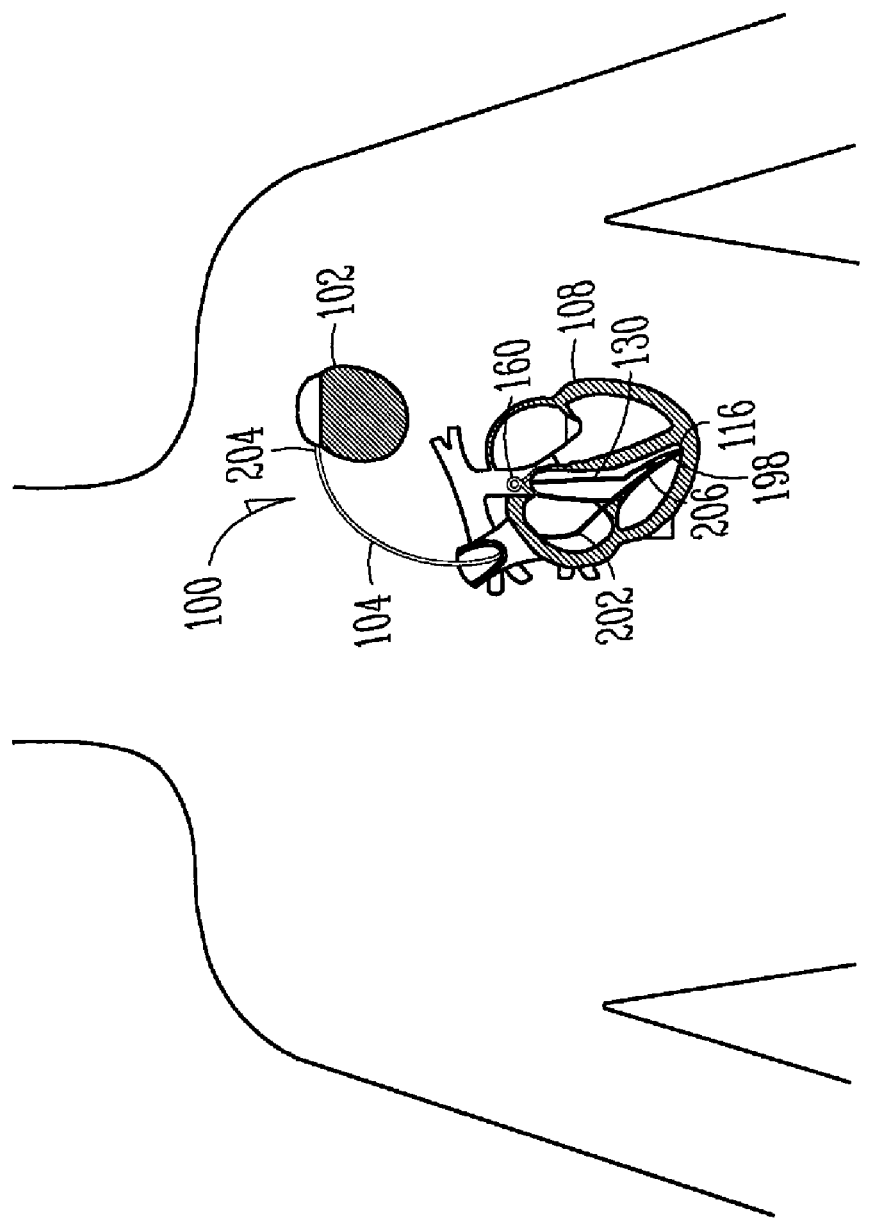
FIG. 1 is a schematic view illustrating an implantable lead system and an environment in which the lead system may be used, as constructed in accordance with at least one embodiment.

FIG. 1 illustrates a lead system 100 and an environment (e.g., a subcutaneous pocket made in the wall of a subject's chest, abdomen, or elsewhere) in which the lead system 100 may be used. In varying examples, the lead system 100 may be used for delivering or receiving electrical pulses or signals to stimulate or sense a heart 108 of a patient. As shown in FIG. 1, the lead system 100 includes an IMD (implantable medical device) 102 and an implantable lead 104. The IMD 102 generically represents, but is not limited to, cardiac function management (referred to as "CFM") systems such as pacers, cardioverters/defibrillators, pacers/defibrillators, biventricular or other multi-site resynchronization or coordination devices such as cardiac resynchronization therapy (referred to as "CRT") devices, sensing instruments, or drug delivery systems.

Among other things, the IMD 102 includes a source of power as well as an electronic circuitry portion. In one example, the electronic circuitry includes microprocessors to provide processing, evaluation, and to determine and deliver electrical shocks or pulses of different energy levels and timing for ventricular defibrillation, cardioversion, or pacing of the heart 108 in response to sensed cardiac arrhythmia including fibrillation, tachycardia, or bradycardia. In another example, the IMD 102 is a battery-powered device that senses intrinsic signals of the heart 108 and generates a series of timed electrical discharges.

The lead 104 includes a lead body 202 extending from a lead proximal end portion 204, where it is couplable with the IMD 102. The lead 104 extends to a lead distal end portion 206, which is positioned within, on, or near tissue to be stimulated, such as a heart 108. In an option, the lead 104 further includes at least one electrode 116 that electrically links the lead 104 with the heart 108. In an option, at least one conductor is disposed within the lead body 202 and electrically couple the at least one electrode 116 with a terminal end of the lead 104 at the lead proximal end portion 204 and the IMD 102. In an option, the lead 104 is a right ventricular lead. In a further option, the lead 104 is a non function right ventricular lead to provide an attachment or anchor to the extended tether.

FIGS. 2A and 2B illustrates an example of a distal portion of the lead 104 in greater detail. The lead 104 includes a lead body 202 and a tether 130 extending therefrom. The tether 130 extends from a proximal tether end portion 132 to a distal tether end portion 134, and having an intermediate portion 136 therebetween. In an option, the tether 130 has an outer diameter substantially less than an outer diameter of the lead body 202. In another option, the tether 130 is substantially more flexible than the lead body 202, allowing for the tether to flow through the heart, as further discussed below. In an example, the tether 130 has an outer diameter of about 3-4 French, and the lead body has an outer diameter of about 6 French. In a further example, the tether has an outer diameter of about 3-4 French, and a single conductor extends therethrough, and the lead body has an outer diameter of about 6 French with multiple conductors extending therethrough.

The tether 130 further includes at least one sensor 160 associated therewith. In an option, the at least one sensor 160 is a pressure sensor. The pressure sensor, in an option, assists in measuring pressure in the pulmonary system. As the lead 104 can be implanted over a longer period of time, the pressure can also be monitored over a longer period of time. In another option, the at least one sensor 160 includes, but is not limited to, at least one of a pressure sensor, a blood chemistry sensor, a blood gas sensor. The pressure sensor can be used to monitor for heart failure, progression of emphysema or pulmonary embolism. In an option, the sensor 160 is disposed at a distal end portion 134 of the tether 130. In a further option, the sensor 160 is wireless operated by an external device, and yet is mechanically held to the lead body 202 by the tether 130. Alternatively, the sensor 160 is hardwired via the lead body 202, where conductors are coupled with the sensor 160 and are disposed within the tether 130.

The tether proximal end portion 132, in an option, is coupled with the distal end portion of the lead body 202. In another option, the tether 130 and the lead body 202 form a generally V-shape. In a further option, an anchor 150 is included at the distal portion of the lead body 202 and at the proximal end portion 132 of the tether 130. In an option, the anchor 150 is a common fixation member to the tether 130 and the lead body 202, and optionally is an active fixation member. In another option, the anchor 150 is a passive fixation member.

The anchor 150 can be used to anchor the lead body 202 into right ventricle wall 180. In another option, the anchor 150 can be fixed proximal to or at the pulmonary outflow tract 182. The sensor 160 tethered by the tether 130, in one option, is disposed in the pulmonary artery 184, in a pre-pulmonic valve location (FIG. 2B). In another option, the sensor 160 is disposed in the pulmonary outflow tract 182, in a post pulmonic valve location (FIG. 2A).

Figure 3A:
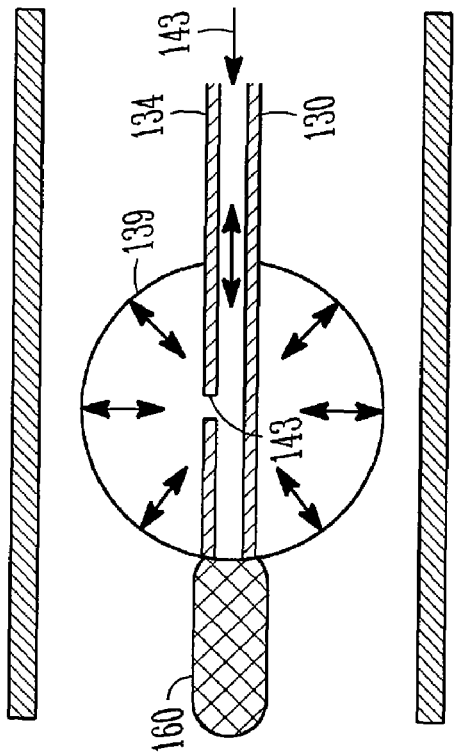
FIG. 3A is a cross-sectional view of a portion of a lead as constructed in accordance with at least one embodiment.
Figure 3B:
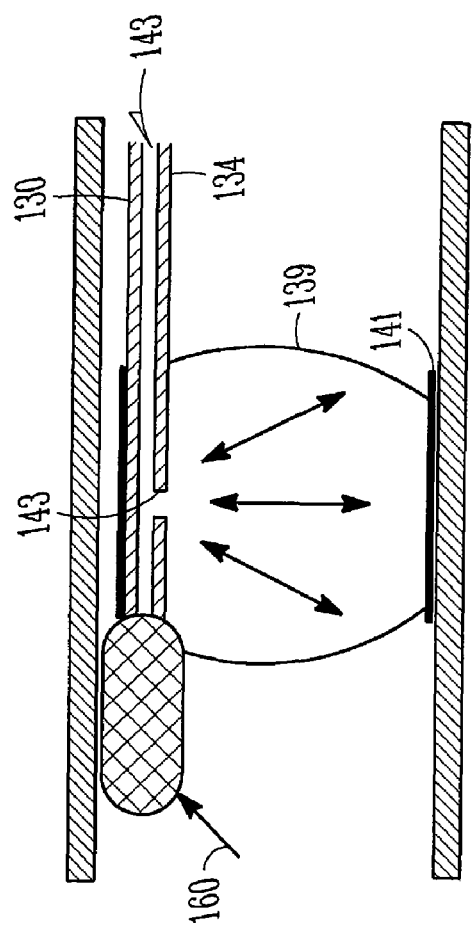
FIG. 3B is a cross-sectional view of a portion of a lead as constructed in accordance with at least one embodiment.

FIGS. 3A and 3B illustrate additional options for the tether 130. For instance, in an option, the distal end portion 134 of the tether 130 includes an anchor, such as an expandable anchor. The anchor can provide a secondary positioning mechanism if local flow patterns cause instability. In an option, the anchor is an expandable balloon 139, as shown in FIG. 3A, or in another option, an acutely collapsible and retractable stent 141, as shown in FIG. 3B. The expandable balloon 139 is manually inflatable, in an option. A fluid passage 143 extends from the balloon 139 to a proximal portion of the lead, where the implanting physician can inject fluid such as a saline based solution to inflate the balloon. The balloon 139, in an option, allows for the lead to be guided by the balloon 139 with the flow of blood through the heart. In a further option, a stent 141 is placed over the balloon 139, as shown in FIG. 3B, and is expandable to maintain the radial position of the sensor. In yet another option, the stent 141 is acutely collapsible and retractable, allowing for retraction of the sensor 160 and tether 130.

FIGS. 4A and 4B illustrate an example for implanting the lead body 202 and the tether 130. In an option, the lead body 202, the tether 130, the sensor 160, and the balloon 139 are at least partially encased in a catheter 190. The catheter 190, including the lead body 202 and the tether 130, are disposed within the heart 108 of the patient and through the right atrium, and through the tricuspid valve 192. In an option, the distal end portion of the lead 202 is placed against the right ventricle wall 180. In a further option, the anchor 150 of the lead body 202 and the tether 130 fixates with the right ventricle wall 180, such as by passive fixation or active fixation, and the catheter is removed to free the tether 130. The balloon 139 is manually inflated with fluid, such as saline solution. Blood flows through the heart from the right atrium to the right ventricle, and eventually to the pulmonary outflow track or the pulmonary artery. As the heart 108 pumps blood therethrough, the tether is pushed by the blood flow from the right atrium toward the pulmonary artery. For example, the sensor 160 of the tether 130 can move to the pulmonary artery 184, as shown in FIG. 2A. In another option, the sensor 160 of the tether 130 can move to the pulmonary outflow tract 182, as shown in FIG. 2B. When the tether 130 further includes a stent 141 (FIG. 3B), the stent 141 can be further expanded by further inflating the balloon 139 when the sensor 160 and balloon 139 is in the designated position. The stent 141 remains expanded and serves as a secondary anchoring mechanism for the sensor 160. The balloon 139 can be deflated and removed.

A method includes disposing a lead body of a lead at a first position within a patient, anchoring the lead body at the first position, flowing a sensor and tether tethered to the lead body to a second position within the patient, measuring a physiological parameter using the sensor at the second position.

In a further option, for example, the balloon 139 is first floated into the pulmonary artery from the right atrium by inflating the balloon and allow the balloon to travel to a wedge position. The balloon is deflated, and a stylet is inserted into the lead. The stylet, in an option, would be stopped at a proximal side of the lead, before the tether 130. The stylet is used to push the portion into the apex of the right ventricle. The portion 198 includes a portion of the lead and a portion of the tether 130, forming a general V-shape. The anchor 150 can fix the general V-shape to the apex, for example, by active fixation. The balloon 150 would free float in the pulmonary artery and allowed to measure for heart failure. For instance, the sensor of the tether can measure for pressure, blood chemistry, blood gas, or a physiological parameter. In an option the pressure sensor can be used to monitor for heart failure, or progression of emphysema or pulmonary embolism. For instance, the pressure measurements from the pulmonary artery and/or wedge pressure measurements can be used to monitor for heart failure, progression of pulmonary embolism or emphysema.

Figure 5:
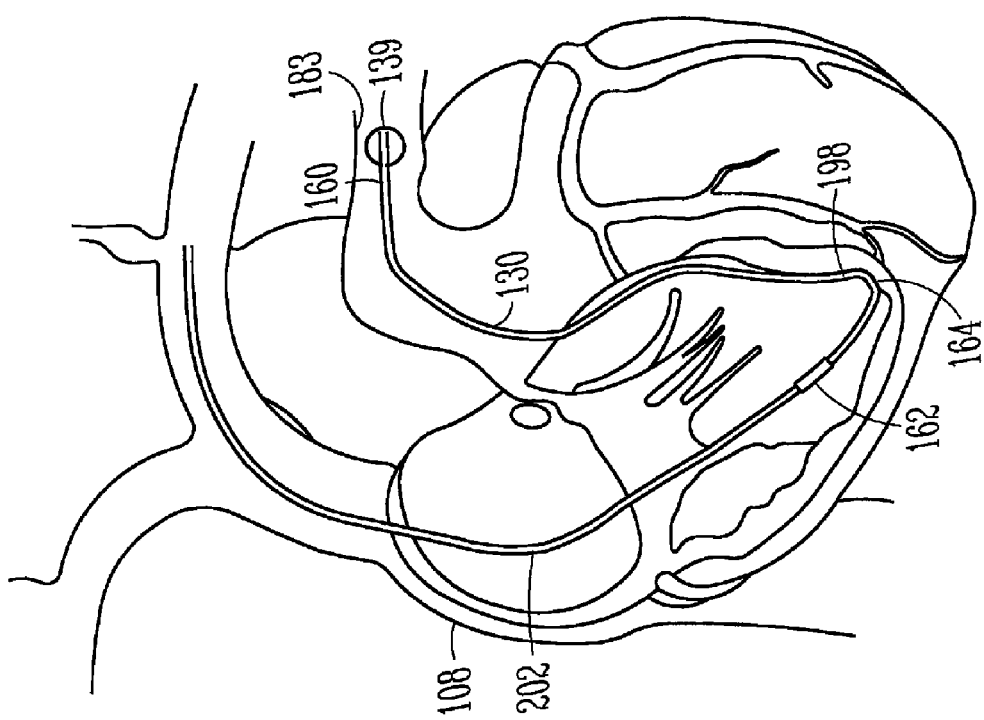
FIG. 5 is a schematic view illustrating an implantable lead system and an environment in which the lead system may be used, as constructed in accordance with at least one embodiment.

FIG. 5 illustrates another example of a lead having a lead body 202 and tether 130. The tether 130 includes, in an option, a narrowed flexible distal extension of the lead. The lead body 202 and tether 130 include the features and options discussed above, such as, but not limited to, the sensor 160, and a balloon anchor 139. In a further option, the tether 130 is coupled with the lead body 202 along a preformed portion 198, such as a V-shaped bend, which optionally resides in an apex of the right ventricle when implanted. Optionally, the tether 130 is integrally formed with the lead body 202, for example, by extrusion.

In a further option, the lead body 202 has an anode 162 and a cathode 164 disposed therealong. Optionally, the anode 162 and the cathode 164 are disposed in the right ventricle. In a further option, the sensor 160, when implanted, is allowed to flow into the left pulmonary artery 183.

Advantageously, the lead and the tether allow for pressure measurement in locations such as, but not limited to, the outflow tract or the pulmonary artery. The deployment is a passive process, making use of the flow of blood through the heart, reducing the level of skill and effort for proper placement. In addition, the sensor follows the flow, and the anchor of the tether would be constrained or self oriented by the tether. As a result, complications of disorientation such as perforations are reduced. Furthermore, the sensor can be retracted from the pulmonary artery through regular removal of the lead.

It is to be understood that the above description is intended to be illustrative, and not restrictive. It should be noted that the above text discusses and figure illustrate, among other things, implantable leads for use in cardiac situations; however, the present leads and methods are not so limited. Many other embodiments and contexts, such as for non-cardiac nerve and muscle situations or for external nerve and muscle situations, will be apparent to those of skill in the art upon reviewing the above description. The scope should, therefore, be determined with reference to the appended claims, along with the full scope of legal equivalents to which such claims are entitled.

What is claimed is:

1. A method comprising:
inserting a stylet into a lead body of a lead and disposing a portion of the lead having a predetermined shape at a first position within a patient;
anchoring the lead body and a tether coupled to the lead body into an apex of the heart at the first position with a common fixation element;
allowing a sensor and the tether to flow to a second position within the patient; and
measuring a physiological parameter using the sensor at the second position, wherein the physiological parameter includes pressure.

2. The method as recited in claim 1, wherein measuring the physiological parameter further includes measuring at least one of blood chemistry or blood gas.

3. The method as recited in claim 1, wherein disposing the sensor at the second position includes disposing the sensor at a right ventricular outflow tract.

4. The method as recited in claim 1, wherein disposing the sensor at the second position includes disposing the sensor in a pulmonary artery.

5. A method comprising:
disposing a lead body of a lead at a right atrium within a patient, the lead including the lead body and a tether coupled with a distal end of the lead body, the lead including a common active fixation element configured to secure both the distal portion of the lead body and a proximal portion of the tether to the heart, the tether having a sensor associated therewith;
inflating a portion of the lead and allowing the tether to float to the pulmonary artery;
actively anchoring the fixation element at a first position in the apex of the right ventricle; and
measuring a physiological parameter using the sensor at a second position, wherein the physiological parameter includes pressure.

6. The method as recited in claim 5, further comprising floating the tether to a wedge position.

7. The method as recited in claim 6, further comprising measuring pressure at the wedge position.

8. The method as recited in claim 6, further comprising deflating the portion of the lead, and relaxing the lead from the wedge position.

9. The method as recited in claim 5, wherein anchoring the lead body at the first position includes anchoring a portion of a V-shaped lead in an apex of the ventricle.

10. The method as recited in claim 9, wherein anchoring the lead includes anchoring the lead in the right ventricle with active fixation.

11. The method as recited in claim 5, further comprising inserting a stylet into the lead and pushing a lead portion having a predetermined shape into an apex of the right ventricle.

12. A cardiac lead comprising:
a lead body having one or more conductors therein, the lead body having a proximal end portion, a distal end portion, and an intermediate portion therebetween;
an electrode disposed along the lead body;
a tether extending from a tether distal end portion to a tether proximal end portion, the tether proximal end portion extending from a distal end of the lead body, the distal end portion of the lead body and the proximal end portion of the tether having a V-shaped configuration configured for anchoring into an apex of the heart; and
a pressure sensor disposed along the tether.

13. The cardiac lead as recited in claim 12, wherein the sensor monitors for heart failure.

14. The cardiac lead as recited in claim 12, wherein the lead body and tether have a common fixation member.

15. The cardiac lead as recited in claim 14, wherein the common fixation member is an active fixation member.

16. The cardiac lead as recited in claim 12, wherein the tether distal end portion includes an anchor.

17. The cardiac lead as recited in claim 16, wherein the anchor is an expandable anchor.

18. The cardiac lead as recited in claim 16, wherein the anchor is an expandable balloon.

19. The cardiac lead as recited in claim 16, wherein the anchor is an acutely collapsible stent at the tether distal end portion.

20. The cardiac lead as recited in claim 12, wherein the sensor is wirelessly operated, and mechanically held by the tether.

* * * * *